(12) United States Patent
Drouin et al.

(10) Patent No.: US 6,210,889 B1
(45) Date of Patent: Apr. 3, 2001

(54) METHOD FOR ENRICHMENT OF FETAL CELLS FROM MATERNAL BLOOD AND USE OF SAME IN DETERMINATION OF FETAL SEX AND DETECTION OF CHROMOSOMAL ABNORMALITIES

(75) Inventors: Regen Drouin; Jean-Claude Forest; Jacques Masse, all of Quebec City (CA)

(73) Assignee: The Universite Laval, Quebec City (CA)

( * ) Notice: Subject to any disclaimer, the term of this patent is extended or adjusted under 35 U.S.C. 154(b) by 0 days.

(21) Appl. No.: 09/238,085

(22) Filed: Jan. 27, 1999

Related U.S. Application Data

(60) Provisional application No. 60/072,911, filed on Jan. 28, 1998.

(51) Int. Cl.[7] .................................................. C12Q 1/68
(52) U.S. Cl. .......................... 435/6; 435/7.1; 435/7.2; 435/7.24; 435/7.25; 435/2; 435/325; 435/366; 435/372
(58) Field of Search .......................... 435/6, 2, 7.1, 7.2, 435/325, 7.25, 7.24, 366; 210/789

(56) References Cited

U.S. PATENT DOCUMENTS

| | | |
|---|---|---|
| 5,422,018 | 6/1995 | Saunders et al. ............... 210/787 |
| 5,432,054 | 7/1995 | Saunders et al. ............... 435/2 |
| 5,437,987 * | 8/1995 | Teng et al. ...................... 435/7.25 |
| 5,447,842 * | 9/1995 | Simons ............................ 435/6 |
| 5,489,386 | 2/1996 | Saunders ......................... 210/5.4 |

FOREIGN PATENT DOCUMENTS

WO 91/16452 * 10/1991 (WO).

OTHER PUBLICATIONS

Herzenberg, L.A., et al.; "Fetal Cells in the Blood of Pregnant Women: Detection and Enrichment by Fluorescence–Activated Cell Sorting"; Proc. Natl. Acad. Sci., USA; Mar. 1979; pp. 1453–1455; vol. 76; No. 3.

Bianchi, D.W.; "Progress in the Genetic Analysis of Fetal Cells Circulating in Maternal Blood"; Current Opinion in Obstetrics and Gynecology; 1997; pp. 121–125; Rapid Science Publishers.

Hawes, C.S., et al.; "A Morphologic Study of Trophoblast Isolated From Peripheral Blood of Pregnant Women"; Am. J. Obstet. Gynecol.; May 1994; pp. 1297–1300; vol. 170; No. 5; Part 1; Mosby–Year Book, Inc.

(List continued on next page.)

*Primary Examiner*—Carla J. Myers
(74) *Attorney, Agent, or Firm*—Oppedahl & Larson LLP

(57) ABSTRACT

An enriched fetal cell sample is prepared from maternal blood by first separating a maternal blood sample on a three layer density gradient, and collection of the layer containing the lymphocytes and a layer immediately beneath the lymphocytes which presumably contains the nucleated fetal red blood cells and low density maternal red blood cells. The top layer in the gradient would contain the plasma and lighter components and the bottom layer would contain high density maternal red blood cells. The collected cells are then placed in a hypotonic solution and centrifuged to separate a fetal cell pellet, which contains enriched levels of fetal cells of varying types. The recovered pellet is fixed twice with Carnoy fixative and the fixed cells are then spread on a slide for FISH analysis.

12 Claims, 1 Drawing Sheet

OTHER PUBLICATIONS

Yeoh, S.C., et al.; "Detection of Fetal Cells in Maternal Blood"; Prenatal Diagnosis; 1991; pp. 117–123; vol. 11; John Wiley & Sons, Ltd.

Holzgreve, W., et al.; "Fetal Cells in the Maternal Circulation"; Journal of Reproductive Medicine; May 1992; pp. 410–418; vol. 37; No. 5; The Journal of Reproductive Medicine, Inc.

Adinolfi, M.; "Non– or Minimally Invasive Prenatal Diagnostic Tests on Maternal Blood Samples or Transcervical Cells"; Prenatal Diagnosis; 1995; pp. 889–896; vol. 15; John Wiley & Sons, Ltd.

Wessman, M., et al.; "Fetal Granulocytes in Maternal Venous Blood Detected by In Situ Hybridization"; Prenatal Diagnosis; 1992; pp. 993–1000; vol. 12; John Wiley & Sons, Ltd.

Ganshirt–Ahlert, D., et al.; "Magnetic Cell Sorting and the Transferrin Receptor as Potential Mean sof Prenatal Diagnosis from Maternal Blood"; Am. J. Obstet. Gynecol.; May 1992; pp. 1350–1355; vol. 166; No. 5.

Price, J.O., et al.; "Prenatal Diagnosis with Fetal Cells Isolated From Maternal Blood by Multiparameter Flow Cytometry"; Am. J. Obstet. Gynecol.; Dec. 1991; pp. 1731–1737; vol. 165; No. 6; Part 1.

Bruch, J.F., et al.; "Trophoblast–Like Cells Sorted from Peripheral Maternal Blood Using Flow Cytometry: A Multiparametric Study Involving Transmission Electron Microscopy and Fetal DNA Amplification"; Prenatal Diagnosis; 1991; pp. 787–798; vol. 11; John Wiley & Sons, Inc.

Mueller, U.W., et al.; "Isolation of Fetal Trophoblast Cells from Peripheral Blood of Pregnant Women"; The Lancet; Jul. 28, 1990; pp. 197–200; vol. 336.

Andrews, K., et al.; "Enrichment of Fetal Nucleated Cells From Maternal Blood: Model Test System Using Cord Blood"; Prenatal Diagnosis; 1995; pp. 913–919; vol. 15; John Wiley & Sons, Ltd.

Ganshirt, D., et al.; "Fetal Cells in Maternal Blood"; Current Opinion in Obstetrics and Gynecology; 1995; pp. 103–108; vol. 7; Current Science Ltd.

Takabayashi, H., et al.; "Development of Non–Invasive Fetal DNA Diagnosis From Maternal Blood"; Prenatal Diagnosis; 1995; pp. 74–77; vol. 15; John Wiley & Sons, Ltd.

Reading, J.P., et al.; "Nucleated Erythrocytes in Maternal Blood: Quantity and Quality of Fetal Cells in Enriched Populations"; Human Reproduction; 1995; pp. 2510–2515; vol. 10; No. 9; Oxford University Press.

Simpson, J.L., et al.; "Isolating Fetal Nucleated Red Blood Cells From Maternal Blood: The Baylor Experience—1995"; Prenatal Diagnosis; 1995; pp. 907–912; vol. 15; John Wiley & Sons, Ltd.

Slunga–Tallberg, A., et al.; "Can Nucleated Erythrocytes Found in Maternal Venous Blood Be Used in the Noninvasive Prenatal Diagnosis of Fetal Chromosome Abnormalities?"; Eur J Hum Genet; 1995; pp. 264–270; vol. 3; S. Karger AG, Basel.

Thomas, M.R., et al.; "The time of Appearance and Disappearance of Fetal DNA From the Maternal Circulation"; Prenatal Diagnosis; 1995; pp. 641–646; vol. 15; John Wiley & Sons, Ltd.

Van Opstal, D., et al.; "A Chromosome 21–Specific Cosmid Cocktail for the Detection of Chromosome 21 Aberrations in Interphase Nuclei"; Prenatal Diagnosis; 1995; pp. 705–711; vol. 15; John Wiley & Sons, Ltd.

Von Koskull, H., et al.; "Fetal Erythroblasts from Maternal Blood Identified with 2,3–Bisphosphoglycerate (BPG) and in situ Hybridization (ISH) Using Y–Specific Probes"; Prenatal Diagnosis; 1995; pp. 149–154; vol. 15; John Wiley & Sons, Ltd.

Zheng, Y., et al.; "Demonstration of Spontaneously Dividing Male Fetal Cells in Maternal Blood by Negative Magnetic Cell Sorting and Fish"; Prenatal Diagnosis; 1995; pp. 573–578; vol. 15; John Wiley & Sons, Ltd.

Zheng, Y., et al.; "Flow Sorting of Fetal Erythroblasts Using Intracytoplasmic Anti–Fetal Haemoglobin: Preliminary Observations on Maternal Samples"; Prenatal Diagnosis; 1995; pp. 897–905; vol. 15; John Wiley & Sons, Ltd.

Durrant, L., et al.; "Non–Invasive Prenatal Diagnosis by Isolation of Both Trophoblasts and Fetal Nucleated Red Blood Cells from the Peripheral Blood of Pregnant Women"; British Journal of Obstetrics and Gynaecology; Mar. 1996; pp. 219–222; vol. 103; RCOG.

Huber, K., et al.; "Development of a Rapid Means of Estimating the Haemoglobin F Content of Candidate Fetal Cells Isolated From Maternal Blood Using HPLC"; Prenatal Diagnosis; 1996; pp. 1011–1019; vol. 16; John Wiley & Sons, Ltd.

Latham, S.E., et al.; "A Monoclonal Antibody to Human Placental Lactogen Hormone Facilitates Isolation of Fetal Cells from Maternal Blood in a Model System"; Prenatal Diagnosis; 1996; pp. 813–821; vol. 16; John Wiley & Sons, Ltd.

Larsen, L.A., et al.; "Quantitative Detection of Male DNA by Polymerase Chain Reaction Using a Single Primer Set; Application to Sex Determination and Counting of Rare Fetal Cells"; Analytical Biochemistry; 1996; pp. 148–150; No. 240; Academic Press, Inc.

Van Wijk, I. J., et al.; "Enrichment of Fetal Trophoblast Cells from the Maternal Peripheral Blood Followed by Detection of Fetal Deoxyribonucleic Acid with a Nested X/Y Polymerase Chain Reaction"; Am. J. Obstet. Gynecol.; 1996; pp. 871–876; vol. 174; No. 3; Mosby–Year Book, Inc.

Wachtel, S. S., et al.; "Fetal Cells in Maternal Blood: Recovery by Charge Flow Separation"; Hum Genet; 1996; pp. 162–166; vol. 98; Springer–Verlag.

Sherer, D. M., et al.; "Noninvasive First–Trimester Screening for Fetal Aneuploidy"; Obstetrical and Gynecological Survey; 1997; pp. 123–129; vol. 52; No. 2; Williams & Wilkins.

Thomas, M. R., et al.; "Y Chromosome Sequence DNA Amplified from Peripheral Blood of Women in Early Pregnancy"; The Lancet; Feb. 12, 1994; pp. 413–414; vol. 343.

Geifman–Holtzman, O., et al.; "Prenatal Genetic Diagnosis by Isolation and Analysis of Fetal Cells Circulating in Maternal Blood"; Seminars in Perinatology; Aug. 1994; pp. 366–375; vol. 18; No. 4; W.B. Saunders Company.

Ganshirt, D., et al.; "Fetal Cells in Maternal Circulation Throughout Gestation"; The Lancet; Apr. 23, 1994; pp. 1038–1039; vol. 343.

Zheng, Y., et al.; "Prenatal Diagnosis from Maternal Blood: Simultaneous Immunophenotyping and FISH of Fetal Nucleated Erythrocytes Isolated by Negative Magnetic Cell Sorting"; J Med Genet; 1993; pp. 1051–1056; vol. 30.

Adkison, L., et al.; "Improved Detection of Fetal Cells from Maternal Blood with Polymerase Chain Reaction"; Am. J. Obstet. Gynecol.; Mar. 1994; pp. 952–955; vol. 170; No. 3; Mosby–Year Book, Inc.

Simpson, J. L., et al.; "Isolating Fetal Cells From Maternal Blood"; JAMA; Nov. 17, 1993; pp. 2357–2361; vol. 270; No. 19.

Shulman, L. P., et al.; "Very Rapid Prenatal Karyotypic Analysis Using Uncultured Fetal Nucleated Red Blood Cells"; Prenatal Diagnosis; 1993; pp. 1153–1156; vol. 13; John Wiley & Sons, Ltd.

Bianchi, D. W., et al.; "Development of a Model System to Compare Cell Separation Methods for the Isolation of Fetal Cells from Maternal Blood"; Prenatal Diagnosis; 1996; pp. 289–298; vol. 16; John Wiley & Sons, Ltd.

Bischoff, F. Z., et al.; "Detection of Low–Grade Mosaicism in Fetal Cells Isolated From Maternal Blood"; Prenatal Diagnosis; 1995; pp. 1182–1184; vol. 15; John Wiley & Sons, Ltd.

Bianchi, D. W., et al.; "Isolation of Fetal DNA From Nucleated Erythrocytes in Maternal Blood"; Proc. Natl. Acad. Sci. USA; May 1990; pp. 3279–3283; vol. 87.

Bhat, N. M., et al.; "One–Step Enrichment of Nucleated Red Blood Cells; A Potential Application in Perinatal Diagnosis"; Journal of Immunological Methods; 1993; pp. 277–280; vol. 159; Elsevier Science Publishers.

Ganshirt–Ahlert, D., et al.; "Detection of Fetal Trisomies 21 and 18 From Maternal Blood Using Triple Gradient and Magnetic Cell Sorting"; American Journal of Reproductive Immunology; 1993; pp. 194–201; vol. 30; Munksgaard, Copenhagen.

Bianchi, D.; "Prenatal Diagnosis by Analysis of Fetal Cells in Maternal Blood"; The Journal of Pediatrics; Dec. 1995; pp. 847–856; vol. 127; No. 6; Mosby–Year Book, Inc.

Mavrou, A., et al.; "Fetal Nucleated Erythrocytes (NRBCS) in Chorionic Villus Sample Supernatant Fluids: An Additional Source of Fetal Material for Karyotype Confirmation"; Prenatal Diagnosis; 1997; pp. 643–649; vol. 17; No. 7; John Wiley & Sons, Ltd.

Rodeck, C., et al.; "Methods for the Transcervical Collection of Fetal Cells During the First Trimester of Pregnancy"; Prenatal Diagnosis; 1995; pp. 933–942; vol. 15; John Wiley & Sons, Ltd.

Adinolfi, M., et al.; "Detection of Fetal Cells in Transcervical Samples and Prenatal Diagnosis of Chromosomal Abnormalities"; Prenatal Diagnosis; 1995; pp. 943–949; vol. 15; John Wiley & Sons, Ltd.

Lichter, P., et al.; "Rapid Detection of Human Chromosome 21 Aberrations by in situ Hybridization"; Proc. Natl. Acad. Sci. USA; Dec. 1988; pp. 9664–9668; vol. 85.

Bergere, M., et al.; "Chromosome 18 Analysis by Fluorescence in situ Hybridization (fish) in Human Blastomeres of Abnormal Embryos After in vitro Fertilization (IVF) Attempt"; Prenatal Diagnosis; 1995; pp. 835–841; vol. 15; John Wiley & Sons, Ltd.

Thangavelu, M., et al.; "Characterization of Marker Chromosomes by Microdissection and Fluorescence in situ Hybridization"; Prenatal Diagnosis; 1994; pp. 583–588; vol. 14; John Wiley & Sons, Ltd.

Pertl, B., et al.; "Rapid Molecular Method for Prenatal Detection of Down's Syndrome"; The Lancet; May 14, 1994; pp. 1197–1198; vol. 343.

Hsieh, T., et al.; "Presence of Fetal Cells in Maternal Circulation After Delivery"; Human Genetics; 1993; pp. 204–205; vol. 92; Springer–Verlag.

Davies, A. F., et al.; "FISH Detection of Trisomy 21 in Interphase by the Simultaneous Use of Two Differentially Labelled Cosmid Contigs"; Medical Genetics; 1994; pp. 679–685; vol. 31.

Martin, R. H., et al.; "Reliability of Aneuploidy Estimates in Human Sperm: Results of Fluorescence In Situ Hybridization Studies Using Two Different Scoring Criteria"; Molecular Reproduction and Development; 1995; pp. 89–93; vol. 42; Wiley–Liss, Inc.

Bryndorf, T., et al.; "New Rapid Test for Prenatal Detection of Trisomy 21 (Down's Syndrome): Preliminary Report"; BMJ; Jun. 13, 1992; pp. 1536–1539; vol. 304.

Pertl, B., et al.; "Rapid Detection of Trisomies 21 and 18 and Sexing by Quantitative Fluorescent Multiplex PCR"; Human Genetics; 1996; pp. 55–59; vol. 98; Springer–Verlag.

Ward, B. E., et al.; "Rapid Prenatal Diagnosis of Chromosomal Aneuploidies by Fluorescence in situ Hybridization: Clinical Experience with 4,500 Specimens"; Am. J. Hum. Genet.; 1993; pp. 854–865; vol. 52; The American Society of Human Genetics.

Spathas, D. H., et al.; "Prenatal Detection of Trisomy 21 in Uncultured Amniocytes by Fluorescence in situ Hybridization: A Prospective Study"; Prenatal Diagnosis; 1994; pp. 1049–1054; vol. 14; John Wiley & Sons, Ltd.

Lewis, D. E., et al.; "Rare Event Selection of Fetal Nucleated Erythrocytes in Maternal Blood by Flow Cytometry"; Cytometry; 1996; pp. 218–227; vol. 23; Wiley–Liss, Inc.

Demaria, M. A., et al.; "Improved Fetal Nucleated Erythrocyte Sorting Purity Using Intracellular Antifetal Hemoglobin and Hoechst 33342"; Cytometry; 1996; pp. 37–45; vol. 25; Wiley–Liss, Inc.

Netten, H., et al.; "FISH and Chips: Automation of Fluorescent Dot Counting in Interphase Cell Nuclei"; Cytometry; 1997; pp. 1–10; vol. 28; Wiley–Liss, Inc.

Nederlof, P. M., et al.; "Quantification of Inter– and Intra––Nuclear Variation of Fluorescence in situ Hybridization Signals"; Cytometry; 1992; pp. 831–838; vol. 13; Wiley–Liss, Inc.

Kibbelaar, R. E., et al.; "Statistical Methods in Interphase Cytogenetics: An Experimental Approach"; Cytometry; 1993; pp. 716–724; vol. 14; Wiley–Liss, Inc.

Carothers, A. D.; "Counting, Measuring, and Mapping in FISH–Labelled Cells: Sample Size Considerations and Implications for Automation"; Cytometry; 1994; pp. 298–304; vol. 16; Wiley–Liss, Inc.

Adinolfi, M., et al.; "Prenatal Detection of Hb Mutations Using Transcervical Cells"; Prenatal Diagnosis; 1997; pp. 539–543; vol. 17; No. 6; John Wiley & Sons, Ltd.

Tutschek, B., et al.; "Isolation of Fetal Cells from Transcervical Samples by Micromanipulation: Molecular Confirmation of Their Fetal Origin and Diagnosis of Fetal Aneuploidy"; Prenatal Diagnosis; 1995; pp. 951–960; vol. 15; John Wiley & Sons, Ltd.

Slunga–Tallberg, A., et al.; "Maternal Origin of Nucleated Erythrocytes in Peripheral Venous Blood of Pregnant Women"; Human Genetics; 1995; pp. 53–57; vol. 96; Springer–Verlag.

Pertl, B., et al.; "Detection of Fetal Cells in Endocervical Samples"; Annals New York Academy of Sciences; pp. 186–192.

Grao, P., et al.; "Appraisal of Fluorescence in situ Hybridization (FISH) Techniques in Prenatal Diagnosis"; Early Human Development; 1993; pp. 101–108; vol. 33; Elsevier Scientific Publishers Ireland, Ltd.

Goodfellow, C. F., et al.; "Extraction and Identification of Trophoblast Cells Circulating in Peripheral Blood During Pregnancy"; British Journal of Obstetrics and Gynaecology; Jan. 1982; pp. 65–68; pp. 65–68; vol. 89; British Journal of Obstetrics and Gynaecology.

Hamada, H., et al.; "Mid–Trimester Fetal Sex Determination From Maternal Peripheral Blood by Fluorescence in situ Hybridization Without Enrichment of Fetal Cells"; Prenatal Diagnosis; 1995; pp. 78–81; vol. 15; John Wiley & Sons, Ltd.

Bianchi, D., et al.; "Erythroid–Specific Antibodies Enhance Detection of Fetal Nucleated Erythrocytes in Maternal Blood"; Prenatal Diagnosis; 1993; pp. 293–300; vol. 13; John Wiley & Sons, Ltd.

Cheuh, J., et al.; "Prenatal Diagnosis Using Fetal Cells From the Maternal Circulation"; Fetal Medicine; The Western Journal of Medicine; 1993; pp. 308–311; vol. 159.

Cacheux, V., et al.; "Detection of 47,XYY Trophoblast Fetal Cells in Maternal Blood by Fluorescence in situ Hybridization after Using Immunographic Lymphocyte Depletion and Flow Cytometry Sorting"; Fetal Diagn Ther; 1992; pp. 190–194; vol. 7; S. Karger AG, Basel.

Hamada, H., et al.; "Fetal Nucleated Cells in Maternal Peripheral Blood: Frequency and Relationship to Gestational Age"; Human Genetics; 1993; pp. 427–432; vol. 91; Springer–Veralg.

Liou, J., et al.; "Fetal Cells in the Maternal Circulation During First Trimester in Pregnancies"; Human Genetics; 1993; pp. 309–311; vol. 92; Springer–Verlag.

Senyei, A. E., et al.; "Fetal Cells in the Maternal Circulation"; Obstetrics and Gynecology Clinics of North America; Sep. 1993; pp. 583–598; vol. 20; No. 3.

Adinolfi, M., et al., "Gene Amplification to Detect Fetal Nucleated Cells in Pregnant Women"; The Lancet; Aug. 5, 1989; pp. 328–329.

Elias, S., et al.; "First Trimester Prenatal Diagnosis of Trisomy 21 in Fetal Cells from Maternal Blood"; The Lancet; Oct. 24, 1992; p. 1033; vol. 340.

Cruz, F., et al.; "Prenatal Diagnosis by use of Fetal Cels Isolated From Maternal Blood"; Am J Obstet Gynecol; Oct. 1995; pp. 1354–1355; vol. 173; No. 4; Mosby–Year Book, Inc.

Bianchi, D.; "Clinical Trials and Experience: Boston"; Annals New York Academy of Sciences; pp. 92–102.

Bianchi, D. W., et al.; "Fetal Cells in Maternal Blood: Determination of Purity and Yield by Quantitative Polymerase Chain Reaction"; Am J Obstet Gynecol; Oct. 1994; pp. 922–926; vol. 171; No. 4; Mosby–Year Book, Inc.

Bigbee, W. L., et al.; "Use of Allele–Specific Glycophorin A Antibodies to Enumerate Fetal Erythroid Cells in Maternal Circulation"; Annals New York Academy of Sciences; pp. 128–132.

Brambati, B.; "Prenatal Diagnosis by Isolating and Analyzing Fetal Nucleated Red Cells: Dream or Reality?"; Annals New York Academy of Sciences; pp. 248–252.

Elias, S., et al.; "Prenatal Diagnosis of Aneuploidy Using Fetal Cells Isolated from Maternal Blood"; Annals New York Academy of Sciences; pp. 80–91.

Ferguson–Smith, M. A., et al.; "Simultaneous IMmunophenotyping and FISH on Fetal Cells from Maternal Blood"; Annals New York Academy of Sciences; pp. 73–79.

Ganshirt, D., et al.; "Successful Prenatal Diagnosis from Maternal Blood with Magnetic–Activated Cell Sorting"; Annals New York Academy of Sciences; pp. 103–114.

Hall, J. M., et al.; "Purification of Fetal Cells from Maternal Blood Using an Avidin–Biotin Immunoaffinity Column"; Annals New York Academy of Sciences; pp. 115–127.

Klinger, K. W.; "FISH: Sensitivity and Specificity on Sorted and Unsorted Cells"; Annals New York Academy of Sciences; pp. 48–56.

Leary, J. F., et al.; "High–Speed Flow Cytometric Analysis and Sorting of Human Fetal Cells from Maternal Blood for Molecular Characterization"; Annals New York Academy of Sciences; pp. 138–141.

Rao, P. N., et al.; "Fluorescence in situ Hybridization on Enriched Nucleated Erythrocytes from Newborn Cord Blood"; Annals New York Academy of Sciences; pp. 142–143.

Liou, J., et al.; "Presence of Cells of Fetal Origin in Maternal Circulation of Pregnant Women"; Annals New York Academy of Sciences; pp. 237–241.

Lo, Y. D.; "Non–invasive Prenatal Diagnosis using Fetal Cells in Maternal Blood"; J Clin Pathol; 1994; pp. 1060–1065; vol. 47.

Sargent, I. L., et al.; "Isolating and Analyzing Fetal Leukocytes in Maternal Blood"; Annals New York Academy of Sciences; pp. 147–153.

Simpson, J. L., et al.; "Fetal Cells in Maternal Blood, Overview and Historical Perspective"; Annals New York Academy of Sciences; pp. 1–8; vol. 731.

Slunga–Tallberg, A., et al.; "Occurrence of Nucleated Erythrocytes in Peripheral Blood of Pregnant Women"; Annals New York Academy of Sciences; pp. 226–228.

Thomas, M. R., et al.; "The Time of Appearance, and Quantitation, of Fetal DNA in the Maternal Circulation"; Annals New York Academy of Sciences; pp. 217–225.

Busch, J., et al.; "Simple and Fast 'Double–MACS' Sorting of Fetal Erythroblasts from Maternal Blood for PCR–Based Paternity Analysis"; Annals New York Academy of Sciences; pp. 144–146.

Sargent, I. L., et al.; "Clinical Experience: Isolating Trophoblasts from Maternal Blood"; Annals New York Academy of Sciences; pp. 154–161.

Lo, Y.D., et al.; "An Improved PCR–Based System for Prenatal Sex Determination from Maternal Peripheral Blood"; Annals New York Academy of Sciences; pp. 214–216.

Lo, Y.D., et al.; "Prenatal Determination of Fetal Rhesus D Status by DNA Amplification of Peripheral Blood of Rhesus–Negative Mothers"; Annals New York Academy of Sciences; pp. 229–236.

Miele, L., et al.; "Development of Novel, Sensitive, Non-radioactive, Quantitative ELISA–PCR Methods Potentially Applicable to the Detection of Fetal Cells in Maternal Circulation"; Annals New York Academy of Sciences; pp. 246–247.

Davies, A. F., et al.; "An Improved Method for the Detection of Trisomy 21 in Uncultured Amniocytes by Fluorescence in situ Hybridization"; Annals New York Academy of Sciences; pp. 67–72.

Beer, A. E., et al.; "The Biological Basis of Passage of Fetal Cellular Material into the Maternal Circulation"; Annals New York Academy of Sciences; pp. 21–35.

Tse, D. B., et al.; "Characterization of Trophoblast–Reactive Monoclonal Antibodies by Flow Cytometry and Their Application for Fetal Cell Isolation"; Annals New York Academy of Sciences; pp. 162–169.

Durrant, L. G., et al.; "Efficient Isolation of Trophoblast Cells from Peripheral Blood"; Annals New York Academy of Sciences; pp. 175–177.

Sbracia, M., et al.; "Possible Use of an Unusual HLA Antigen to Select Trophoblast Cells from the Maternal Circulation to Perform Early Prenatal Diagnosis"; Annals New York Academy of Sciences; pp. 170–174.

Yang, Y., et al.; "Anti–Trophoblast Monoclonal Antibodies for Prenatal Genetic Diagnosis"; Annals New York Academy of Sciences; pp. 178–180.

Hawes, C. S., et al.; "Detection of Paternally Inherited Mutations for B–Thalassemia in Trlphoblast Isolated from Peripheral Maternal Blood"; Annals New York Academy of Sciences; pp. 181–185.

Lo, Y. D., et al.; "Strategies for the Detection of Autosomal Fetal DNA Sequence from Maternal Peripheral Blood"; Annals New York Academy of Sciences; pp. 204–213.

Park, V. M., et al.; "A Model System Using Fetal Hemoglobin to Distinguish Fetal Cells Enriched from Maternal Blood"; Annals New York Academy of Sciences; pp. 133–135.

* cited by examiner

METHOD FOR ENRICHMENT OF FETAL CELLS FROM MATERNAL BLOOD AND USE OF SAME IN DETERMINATION OF FETAL SEX AND DETECTION OF CHROMOSOMAL ABNORMALITIES

This application is filed under 35 USC § 111(a) and claims priority under 35 USC § 119(e) from U.S. Provisional Patent Application No. 60/072,911 filed Jan. 28, 1998.

BACKGROUND OF THE INVENTION

This application relates to a method and kit for isolation of fetal cells from maternal blood and to the use of same in detection of chromososomal abnormalities.

Numerical chromosomal abnormalities, particularly those in chromosomes 21, 18 and 13 and the X and Y chromosomes account for a significant portion of the genetic defects in liveborn human beings. For this reason, prenatal testing for such abnormalities is carried out in some instances, particularly where the fetus is within a high-risk group. Unfortunately, the most reliable tests involve invasive procedures, such as amniocentesis, which themselves pose some risk to the pregnancy and to the fetus. Furthermore, the cost of the procedure is substantial, which adds an additional factor to the more appropriate balancing of risk to the fetus against the likelihood of that an abnormality will be detected. Thus, it would be desirable to be able to perform reliable testing for chromosomal abnormalities using a noninvasive technique.

The existence of fetal cells in the maternal circulation has been the topic of considerable research and testing over many years. It is now understood that there are three principal types of fetal cells: lymphocytes, trophoblasts and nucleated fetal erythrocytes. These cell types are found in variable, although always very small numbers and at various times within maternal blood. Holgreve et al., "Fetal Cells in Maternal Circulation", *J. Reproductive Med.* 37: 410–418 (1992). Various proposals have been advanced for the isolation or enrichment of one or another of these cells types from a maternal blood sample, and it has been proposed to use these isolated or enriched cells for testing for chromosomal abnormalities.

Fetal cells have been enriched from maternal blood using antibody capture techniques in which an immobilized antibody that binds to fetal cells captures the fetal cells to facilitate their enrichment. Mueller et al., "Isolation of fetal trophoblasts cells from peripheral blood of pregnant women", *The Lancet* 336: 197–200 (1990); Gänshirt-Ahlert et al., "Magnetic cell sorting and the transferring receptor as potential means of prenatal diagnosis from maternal blood" *Am. J. Obstet. Gynecol.* 166: 1350–1355 (1992). Fetal cells have also been labeled with antibodies and other specific binding moieties to facilitate cell sorting procedures such as flow cytometry. Herzenberg et al., "Fetal cells in the blood of pregnant women: Detection and enrichment by fluorescence-activated cell sorting", *Proc. Natl Acad. Sci. (USA)* 76: 1453–1455 (1979); Bianchi et al., "Isolation of fetal DNA from nucleated erythrocytes in maternal blood" *Proc. Natl Acad. Sci. (USA)* 87: 3279–3283 (1990); Bruch et al., "Trophoblast-Like cells sorted from peripheral maternal blood using flow cytometry: a multiparametric study involving transmission electron microscopy and fetal DNA amplification" *Prenatal Diagnosis* 11: 787–798 (1991). Price et al. "Prenatal diagnosis with fetal cells isolated from maternal blood by multiparameter flow cytometry" *Am. J. Obstet. Gynecol* 165: 1731–1737 (1991). PCR techniques have also been proposed to increase the relative amount of fetal DNA to permit analysis. Bianchi et al., "Isolation of fetal DNA from nucleated erythrocytes in maternal blood", *Proc. Natl Acad. Sci (USA)* 87: 3279–3283 (1990); Adkinson et al., "Improved detection of fetal cells from maternal blood with polymerase chain reaction", *Am. J. Obstet. Gynecol.* 170: 952–955 (1994); Takabayashi et al., "Development of non-invasive fetal DNA diagnosis from maternal blood" *Prenatal Diagnosis* 15: 74–77 (1995).

Gradient centrifugation plays a role as a preliminary step in many of these known techniques for isolation or enrichment of fetal cells. U.S. Pat. No. 5,432,054 also describes a technique for separation of rare cells, specifically fetal nucleated red blood cells, using gradient centrifugation. In this technique, maternal blood is centrifuged in a tube having a wide top and a narrow, capillary bottom made of polyethylene, using a variable speed program which results in a stacking of red blood cells in the capillary based on density. The density fraction containing low density red blood cells (which should include any fetal cells) is recovered and then differentially hemolyzed to preferentially destroy maternal red blood cells. The hemolyzed material is then separated on a density gradient in a hypertonic medium prepared from variable amounts of a colloid (which imparts the density variation) dispersed in a meltable gel to separate red blood cells, now enriched in the fetal red blood cells from lymphocytes and ruptured maternal cells. The use of a hypertonic solution shrinks the red blood cells, making them more dense relative to lymphocytes and thus easier to separate.

The method of U.S. Pat. No. 5,432,054 in theory offers a simple approach to the preparation of enriched fetal cell preparations from maternal blood. Unfortunately, in practice trials on cell preparations made using this method have been unable to identify aneuploid chromosomal abnormalities at rates that are significantly better than random chance. Elias, S., "Multicenter NIH Clinical Trials on Fetal Cells in Maternal Blood: Description and Current Status", *Am. J. Hum. Genet.* 61 (suppl): 29 (1997)( results presented orally at the 47th Annual meeting of the American Society of Human Genetics, Baltimore, Md. in October, 1997). Thus, there remains a need for a method for preparing enriched fetal cells which is simple to perform, and which nonetheless provides a preparation which can be reliably used to determine genetic information about the fetus. It is an object of the present invention to provide such a method.

SUMMARY OF THE INVENTION

In accordance with the present invention, an enriched fetal cell sample is prepared from maternal blood by first separating a maternal blood sample on a three layer density gradient, and collection of the layer containing the lymphocytes and a layer immediately beneath the lymphocytes which presumably contains the nucleated fetal red blood cells and low density maternal red blood cells. The top layer in the gradient would contain the plasma and lighter components and the bottom layer would contain high density maternal red blood cells. The collected cells are then placed in a hypotonic solution and centrifuged to separate a fetal cell pellet, which contains enriched levels of fetal cells of varying types. The recovered pellet is fixed twice with Carnoy fixative and the fixed cells are then spread on a slide for FISH analysis.

DETAILED DESCRIPTION OF THE INVENTION

Figure 1:
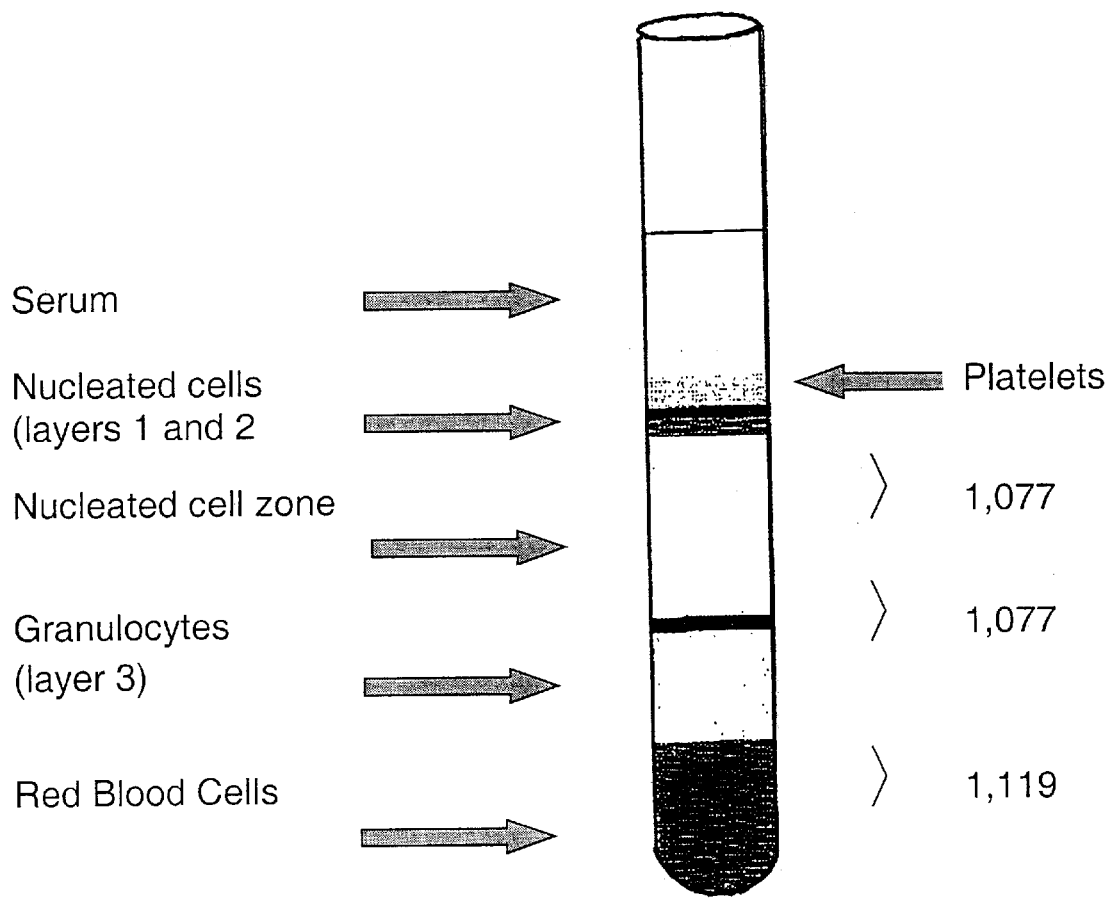
FIG. 1 shows the separation of maternal blood cells achieved using a three layer gradient in the method of the invention.

The first step of method of the present invention is the separation of a maternal blood sample on a three-layer density gradient. The maternal blood sample may be taken at any time between the sixth and thirty-fifth weeks of pregnancy, preferably between the twelfth and fourteenth weeks. In general, a sample volume of at least 10 ml is desirable, although volumes between 2 and 40 ml are generally suitable.

The maternal blood sample is preferably processed within the first one to three hours after sample collection. If the processing is delayed beyond three hours, the sample should be stored at 4° C. until processed.

The gradient used for separation of the cells of the maternal blood sample is a three-level gradient which separates the cells into fractions as illustrated in FIG. 1. A suitable gradient to achieve this result can be made from ficoll "histopaque." Three layers are formed by carefully pipetting equal volumes of ficoll solutions having densities of 1.119, 1.107 and 1.077 gm/ml into a tube. The gradient is allowed to rest for several minutes prior to application of the maternal blood sample. The sample is stilled just before addition to the gradient to prevent agglutination.

For a three layer ficoll gradient formed as above with 2 ml fractions at each density in a 15 ml tube, a 10 ml sample of maternal blood is suitably used. The gradient is then centrifuged at 1500 RPM (about 500×g) for 30 minutes in a swinging bucket centrifuge to achieve separation as shown in FIG. 1. As shown, after centrifugation, nucleated cells are stacked at the level of layers 1 and 2 and granulocytes are found at the level of layer 3. Between these layers there is a nucleated cell zone. The layer of lymphocytes (layer 1) and the layer directly beneath the lymphocytes (layer 2) are collected, while avoiding the layer over the 1.107 density line. This results in the collection of a cell fraction in which all different types of fetal cells are enriched.

Other gradient materials and densities can be used, provided that they result in substantially the separation pattern shown in FIG. 1. For example, density gradients formed from percoll, sucrose, polyethylene glycol and chlorofluorocarbons might also be used. Other types of gradients might be employed, including osmolarity gradients, pH gradients, magnetic field gradients, viscosity gradients and conductivity gradients. Materials which might be included in such gradients include acrylamide, agarose, Sephadex, dextran, ion exchange substances riboflavine, cryoprotective substances, phosphate buffered solution, DMSO, metrizamide, nycoprep, chromophobs, iodixanol, saline solution, proteins and oils.

The collected cells are transferred into a 15 ml tube containing 3 ml Hank's Balanced Salt Solution (HBSS) at room temperature, after which the volume is increased to 12 ml with HBSS for washing the cells. The cells and the HBSS are mixed by inversion and centrifuged at 1500 RPM (about 500×g, Centrifuge ICE, model HN SII). The platelet-rich supernatant is discard and the pellet of maternal blood cells is resuspended in 0.56% KCl at 37° C. to a total volume of 12 ml while vortexing at minimum speed. This mixture is incubated for 5 minutes at 37° C. and centrifuged for 5 minutes at 2000 RPM (about 600–650×g, Model HN SII). The pelleted cells are recovered and fixed twice by suspending in 12 ml Carnoy fixative (methanol: acetic acid—2:1) while vortexing at minimum speed and then recovering by centrifugation at 600–550×g.

After the second fixation is completed, the cells are spread on a clean slide (cleaned by soaking overnight in etha-nol:chloric acid—9:1, rinsing with tap water for 2 hours, followed by three successive 5 minute rinses of distilled water and three 5 minute rinses in 100% ethanol) for analysis by Fluorescence In-Situ Hybridization (FISH) using an appropriate oligonucleotide probe. The spreading is preferably done under conditions of controlled temperature and humidity, for example in a THERMOTRON at 25° C. and 36% humidity. A heated water bath at 60° C. containing a slide support standing about one inch above the water can also be used. After spreading and drying, the slides are placed in an incubator at 37° C. overnight.

The cells prepared in this way are used for evaluation of the genetic composition of fetal cells using the FISH technique and a fluorescently-labeled nucleic acid probe specific for the condition of interest, and is limited only by the availability of a probe for FISH analysis that is specific to a particular chromosomal abnormality. In particular, the prepared cells can be utilized for determination of fetal sex, detection of Trisomy 21 (Down's Syndrome), Trisomy 18, Trisomy 13 and other numerical chromosome abnormalities by selection of an appropriate FISH probe. The techniques employed for this determination are standard in the art, although we have found that the best results are obtained using VYSIS probes which are directly labeled with fluorescent tag. Probes labeled with *SPECTRUMAQUA* fluorescent label give the best results, but other fluorochromes such as *SPECTRUMORANGE* also give good results.

In the FISH technique, the slide is incubated with warm 2× salt saline citrate solution (1×SSC=150 mM NaCl and 15 mM Na citrate) for 30 minutes and then dehydrated by passing through successive solutions of 70%, 80% and 100% ethanol. The slide is then immersed in a denaturant solution (70% formamide/2× SSC) for two minutes and dehydrated again with ethanol. After air drying, 10 ul of probe mix (labeled probe in hybridization buffer) is place don the slide an incubated for 4 to 16 hours. The slide is then washed with 50% formamide/2× SSC for 5 minutes, followed by 2× SSC for five minutes and a brief wash with 2× SSC/0.1% NP-40. The slide is then counterstained with DAPI II (Vysis) and sealed with a coverslip until examination under a fluorescence microscope.

The cell preparations made in accordance with the invention are very well suited for use in FISH analysis. Usually, for FISH analysis of interphase nuclei, a background (false positive signal) of one nucleus per 1000 nuclei is considered to be very good. The enrichment method of the invention is very gentle on the cells, and recovers all types of fetal cells in the maternal circulation. This results in a decrease in the background to levels of 0 to 3 false positive signals per $1 \times 10^5$ nuclei, an approximately one-hundred fold improvement.

While the process of the invention is described above by way of a preferred embodiment, there are variations which may be made without departing from the scope of the invention. Thus, for example, the gradient can be made with two layers, or with more layers (e.g. up to five layers) to further refine the separation of cells. In addition, the cells may be processed through the gradient several times (e.g. 2 to 5 times) to achieve higher levels of enrichment.

The reagents and materials for preparing an enriched fetal cell sample in accordance with the present invention can be packaged in the form of a kit to facilitate practice of the invention. Such a kit will include the appropriate solutions, and may include a preformed gradient, such as those disclosed in U.S. Pat. No. 5,432,054.

EXAMPLE 1

Using the method of the invention, 25 samples of maternal blood were evaluated to determine fetal sex. In 24 of these samples (96%), the sex of the fetus was correctly determined.

EXAMPLE 2

Using the method of the invention, 5 samples of maternal blood were evaluated to identify the type of trisomy. Three cases of trisomy 21, one case of trisomy 13 and one case of trisomy 18 were correctly identified.

What is claimed is:

1. A method for preparing fetal cells for analysis by fluorescence in-situ hybridization consisting essentially of the steps of:
   (a) obtaining a maternal blood sample;
   (b) separating the maternal blood sample on a gradient in one or more passes, and collecting a layer containing lymphocytes and a layer immediately beneath the lymphocytes which contains fetal red blood cells;
   (c) placing the collected cells in a hypotonic solution and centrifuging to separate a red blood cell pellet which contains fetal red blood cells;
   (d) recovering the red blood cell pellet and fixing the cells in the recovered pellet twice; and
   (e) spreading the fixed cells on a slide for analysis by fluorescence in-situ hybridization.

2. The method of claim 1, wherein the gradient is a density gradient.

3. The method of claim 2, wherein the density gradient is a three layer gradient.

4. The method according to claim 3, wherein the density gradient is a ficoll gradient.

5. The method according to claim 3, wherein the three layers of the density gradient have densities of 1.119, 1.107 and 1.077 gm/ml.

6. The method according to claim 5, wherein the density gradient is a ficoll gradient.

7. The method according to claim 1, wherein the cells are fixed with Carnoy fixative.

8. A method for determining fetal sex comprising the step of:
   (a) obtaining a sample of maternal blood;
   (b) preparing an enriched sample in which the number of fetal cells is enriched relative to the number of maternal cells from the sample of maternal blood by a method consisting essentially of the steps of
      (i) separating the maternal blood sample on a gradient in one or more passes, and collecting a layer containing lymphocytes and a layer immediately beneath the lymphocytes which contains fetal red blood cells;
      (ii) placing the collected cells in a hypotonic solution and centrifuging to separate a red blood cell pellet;
      (iii) recovering the red blood cell pellet and fixing the cells in the recovered pellet twice; and
      (iv) spreading the fixed cells on a slide for analysis; and
   (c) evaluating the fixed cells spread on the slide by fluorescence in-situ hybridization to determine fetal sex.

9. The method of claim 8, wherein the gradient is a density gradient.

10. A method for determining the presence of fetal aneuploidies comprising the step of:
    (a) obtaining a sample of maternal blood;
    (b) preparing an enriched sample in which the number of fetal cells is enriched relative to the number of maternal cells from the sample of maternal blood by a method consisting essentially of the steps of
       (i) separating the maternal blood sample on a gradient in one or more passes, and collecting a layer containing lymphocytes and a layer immediately beneath the lymphocytes which contains fetal red blood cells;
       (ii) placing the collected cells in a hypotonic solution and centrifuging to separate a red blood cell pellet;
       (iii) recovering the red blood cell pellet and fixing the cells in the recovered pellet twice; and
       (iv) spreading the fixed cells on a slide for analysis;
    (c) evaluating the fixed cells spread on the slide by fluorescence in-situ hybridization to determine the presence of fetal aneuploidies.

11. The method of claim 10, wherein the gradient is a density gradient.

12. The method according to claim 10, wherein the fluorescence in-situ hybridization detects the presence of Trisomy 21.

* * * * *